(12) United States Patent
Huang et al.

(10) Patent No.: US 9,248,430 B2
(45) Date of Patent: Feb. 2, 2016

(54) METHOD FOR SYNTHESIS OF 1-DECENE OLIGOMER

(75) Inventors: Fuling Huang, Daqing (CN); Puke Mi, Shanghai (CN); Sihan Wang, Daqing (CN); Jinhua Qian, Beijing (CN); Qian Chen, Daqing (CN); Sheng Xu, Shanghai (CN); Jianzhong Li, Daqing (CN); Gang Wang, Daqing (CN); Baojun Zhang, Daqing (CN); Min Liu, Shanghai (CN); Guizhi Wang, Daqing (CN); Xuemei Han, Daqing (CN); Jiabo Qu, Daqing (CN); Panfeng Lu, Shanghai (CN); Shukun Sun, Daqing (CN); Xiuhui Wang, Daqing (CN); Yuxin Gao, Daqing (CN); Deshun Zhang, Daqing (CN); Ling Jiang, Shanghai (CN); Buwei Yu, Daqing (CN); Libo Wang, Daqing (CN); Yali Wang, Daqing (CN); Lingting Fan, Shanghai (CN); Peng Wei, Shanghai (CN); Wei Liu, Shanghai (CN); Guiyue Guo, Daqing (CN)

(73) Assignees: PETROCHINA COMPANY LIMITED (CN); EAST CHINA UNIVERSITY OF SCIENCE (CN)

( * ) Notice: Subject to any disclaimer, the term of this patent is extended or adjusted under 35 U.S.C. 154(b) by 754 days.

(21) Appl. No.: 13/510,216

(22) PCT Filed: Jul. 22, 2010

(86) PCT No.: PCT/CN2010/001110
§ 371 (c)(1),
(2), (4) Date: May 16, 2012

(87) PCT Pub. No.: WO2011/060606
PCT Pub. Date: May 26, 2011

(65) Prior Publication Data
US 2012/0232321 A1 Sep. 13, 2012

(30) Foreign Application Priority Data
Nov. 17, 2009 (CN) .......................... 2009 1 0238205

(51) Int. Cl.
*C07C 6/10* (2006.01)
*B01J 21/04* (2006.01)
*B01J 37/02* (2006.01)
*C07C 2/22* (2006.01)

(52) U.S. Cl.
CPC .............. *B01J 21/04* (2013.01); *B01J 37/0205* (2013.01); *B01J 37/0207* (2013.01); *C07C 2/22* (2013.01); *C07C 2521/04* (2013.01); *C07C 2527/126* (2013.01)

(58) Field of Classification Search
CPC .... B01J 37/00; B01J 37/0201; B01J 37/0236; B01J 37/08; B01J 37/24
USPC .......................................... 585/643; 502/231
See application file for complete search history.

(56) References Cited

U.S. PATENT DOCUMENTS

| 2,927,087 | A |   | 3/1960  | Smith                       |
|-----------|---|---|---------|-----------------------------|
| 2,939,848 | A | * | 6/1960  | Malo et al. ......... 502/334 |
| 3,480,389 | A | * | 11/1969 | Graulier ............. 423/626 |
| 4,929,800 | A |   | 5/1990  | Drago et al.                |
| 5,136,118 | A | * | 8/1992  | Buchanan et al. ..... 585/255 |
| 5,451,704 | A | * | 9/1995  | Ho ............... B01J 37/0215 |
|           |   |   |         |                     502/113 |
| 6,002,060 | A |   | 12/1999 | Sarin et al.                |

FOREIGN PATENT DOCUMENTS

| CH | 200610047647.5 |   | 4/2007 |
| CN | 96113183.7     |   | 8/1997 |
| CN | 1939590 A      | * | 4/2007 |
| JP | 8-505888       |   | 6/1996 |

OTHER PUBLICATIONS

Drago, R. S.; Getty. E. E. "Preparation, Characterization, and Catalytic Activity of a New Solid Acid Catalyst System" Inorg. Chem. (1990), 29, 1186-1192.*
Haynes, CRC Handbook of Chemistry and Physics, 95th edition, 2014 Internet Version, W. M. Haynes, editor—month unknown.*
International Search Report corresponding to PCT/CN2010/001110 dated Oct. 28, 2010.

* cited by examiner

*Primary Examiner* — Renee E Robinson
*Assistant Examiner* — Aaron Pierpont
(74) *Attorney, Agent, or Firm* — Locke Lord LLP; Alan B. Clement; Peter J. Fallon

(57) ABSTRACT

A method for synthesis of 1-decene oligomer is provided, wherein 1-decene is polymerized at 80-120° C., 0.8-1.4 MPa in the presence of aluminum trichloride catalyst supported on gamma-alumina and n-hexane solvent where the volume ratio of 1-decene to n-hexane is 3:8-4:1. The catalyst is treated as follows: impregnating gamma-alumina carrier in 0.5-2.0 M of hydrochloric acid, sulfuric acid, nitric acid or mixtures thereof, then vacuum drying at 80-100° C. and calcining at 400-800° C.; dissolving 5-10 g of anhydrous aluminum trichloride in 100 ml of tetrachloromethane, trichloromethane or dichloromethane solvent; adding the obtained solution into 10-20 g of activated alumina carrier and obtaining the catalyst after vacuum drying. The conversion of 1-decene is 50 wt % or more. The oligomer has a kinematic viscosity at 40° C. of 6.0-25 $mm^2/s$ and a viscosity index of 160-262.

6 Claims, No Drawings

METHOD FOR SYNTHESIS OF 1-DECENE OLIGOMER

CROSS-REFERENCE TO RELATED APPLICATIONS

This application is a national phase application, under 35 U.S.C. 371, of international application No. PCT/CN2010/001110, filed on Jul. 22, 2010, which claimed priority to Chinese Patent Application No. CN 200910238205.2, filed on Nov. 17, 2009, the disclosures of which are incorporated herein by reference.

FIELD OF THE INVENTION

The present invention relates to use of a catalyst, aluminum trichloride supported on gamma-alumina, in the catalysis of 1-decene oligomerization.

BACKGROUND OF THE INVENTION

As a Lewis acid catalyst used in cationic polymerization, $AlCl_3$ catalyst is one of the important catalysts widely used chemical industry, petroleum refining and pharmaceutical industry. Due to good catalytic effect, such catalysts have features such as high polymer yield, narrow molecular weight distribution and good selectivity in the catalysis of α-olefin oligomerization. Although it has very high activity, $AlCl_3$ catalyst has obvious disadvantages as follows: (1) $AlCl_3$ catalyst has strong causticity, which may easily cause damage to equipments such as reaction kettles and thus reduce service life of the equipment, leading to less usage; (2) a large quantity of wastewater is produced during the polymerization in the presence of $AlCl_3$ catalyst, thus severe environmental pollution will be caused if the wastewater cannot be disposed in time; and (3) $AlCl_3$ catalyst after reaction cannot be easily recovered such that numerous corrosive waste is produced, thus a post-treatment process becomes necessary.

JP 08505888B discloses a method for producing lubricant base oil through cationic polymerization, wherein decene polymer is produced in the presence of Lewis acid such as $AlCl_3$, $BF_3$ as the catalyst. Since a homogeneous system is used in the method, resulting in a high amount of halide such as $AlCl_3$, $BF_3$ in product, products having a low level of halide cannot be produced. What is more, $BF_3$ is both expensive and easy to cause a series of environmental problems due to the corrosivity of fluorine. Since such catalysts are difficult to be separated and are hardly recycled while a number of troublesome industrial waste liquid is produced, the cost of production is increased. Meanwhile, the α-olefin polymer thus obtained has a low molecular weight, and the obtained lubricant thus has a low viscosity, which cannot meet the environmental requirement when used as a lubricant.

Therefore, in order to satisfy the requirement of green chemistry, solid acid catalysts such as supported metal oxide are developed to replace traditional catalysts such as $AlCl_3$ and $BF_3$, meanwhile immobilized $AlCl_3$ catalysts are also studied widely. It is desirable to eliminate the current problems as above and convert the $AlCl_3$ catalyst into an environmentally friendly catalyst, providing that the excellent characteristics of $AlCl_3$ can be maintained. A supported $AlCl_3$ catalyst is a novel, efficient and environmentally friendly solid acid catalyst. In recent years, it has attracted more attention due to its higher catalytic activities and mild reaction conditions, and is widely used in the research on polymerization and alkylation.

U.S. Pat. No. 2,927,087 firstly proposes a method for producing a supported $AlCl_3$ catalyst by the reaction of $AlCl_3$ vapor with infusible oxides such as alumina and silica having a hydroxyl group on the surface thereof. Moreover, it emphasizes the necessity to remove unreacted $AlCl_3$ by purging carrier gas above 300° C. after the reaction.

U.S. Pat. No. 4,929,800 discloses that a catalyst with high activity in the isomerization or pyrolysis of alkanes can be produced by a process of dissolving aluminum trichloride in a solvent such as $CCl_4$, $CH_3Cl$ or $CH_2Cl_2$, adding a carrier such as silica or alumina thereto, and refluxing the resultant at 50-80° C. under $N_2$ protection and dark condition refluxing for several hours to days.

U.S. Pat. No. 6,002,060 indicates that alpha-olefin can be oligomerized or copolymerized in the presence of supported aluminum trichloride as a catalyst and an organic aluminum compound as an aid.

CN 1156338 and CN 1939590 disclose that immobilized $AlCl_3$ catalysts are prepared by the gas-phase immobilization as follows: reacting fresh aluminum trichloride carried by $N_2$ gas brought into a reaction tube having alumina with a double-pore structure of mesopore and macropore and a particles size of 20-200 mesh therein, wherein the chlorine content is 6.0-9.0 wt %. The catalysts have shown good catalytic activity and selectivity in isobutene polymerization of low degree, and exhibit good stability. However, noticeable pressure drop is observed in the reaction of a fixed bed reactor filled with catalysts in form of fine particles.

SUMMARY OF THE INVENTION

The present application is aimed at providing use of a catalyst, aluminum trichloride supported on gamma-alumina, in the catalysis of 1-decene oligomerization. The supported catalyst has a high activity in the catalysis of 1-decene oligomerization, and can be easily separated from the reaction product. Thus, the catalyst can be recovered and recycled, reducing pollution to environment. Furthermore, the catalyst can avoid not only the corrosion to the reactor caused by a homogenous catalyst, but also the presence of halide in the product of 1-decene oligomerization.

The catalyst of the present application is prepared as follows:

1) a step of acidifying and impregnating a gamma-alumina carrier, comprising:

in particular, impregnating a gamma-alumina carrier in a 0.5-2.0 M solution of hydrochloric acid, sulfuric acid, nitric acid or mixtures thereof at room temperature for 4-12 hours, then vacuum drying at 80-100° C. for 2-12 hours and finally calcinating at 300-800° C. for 6-16 hours;

2) a step of immobilizing aluminum trichloride in a solution, comprising:

dissolving 5-10 g of anhydrous aluminum trichloride in 100 ml of an organic solvent such as tetrachloromethane, trichloromethane or dichloromethane to prepare a solution, into which 10-20 g of the activated alumina carrier is added, then refluxing at reflux temperature for 6-24 hours, and further removing the solvent, washing with n-hexane, and vacuum drying to obtain the catalyst, aluminum trichloride supported on gamma-alumina.

In the preparation of the catalyst according to the present application, the gamma-alumina carrier is a sphere-shaped or strip-shaped alumina carrier. The sphere-shaped gamma-alumina carrier has a diameter of 1.3-2.3 mm, preferably 1.5-2.0 mm, a specific surface area of 100-180 $m^2/g$, preferably 120-160 $m^2/g$, and a total pore volume of 1.0 ml/g or more. The trip-shaped carrier has a diameter of 3 mm, a length of 4-10 mm, preferably 5-8 mm, a specific surface area of 100-200 $m^2/g$, preferably 140-180 $m^2/g$, and a total pore volume of 0.6 ml/g or more.

The gamma-alumina carrier is acidified by using, most preferably, hydrochloric acid having an optimum concentration of 1 M for an optimum impregnating time of 6 hours, and calcinated at an optimum calcination temperature of 400° C. for a calcination time of 12 hours.

In the preparation of the catalyst according to the present application, the solvent for immobilizing anhydrous aluminum trichloride is, most preferably, tetrachloromethane or a mixed solvent of tetrachloromethane and trichloromethane in a volume ratio of 1:1, and the reflux lasts preferably for a period of 12 hours.

Using the process for preparing the supported catalyst according to the present application, the supported aluminum trichloride catalyst as finally fabricated has a chlorine content of 6.0-12 wt %. That is, the supported catalyst contains —$AlCl_2$ in a weight ratio of 8.28-16.56 wt %.

In the preparation of the catalyst, aluminum trichloride supported on alumina, all of the reactions are carried out under protection of inert gas such as nitrogen or argon.

The supported catalyst according to the present invention can be applied in the catalysis of 1-decene oligomerization to produce 1-decene oligomer. The principle is believed to be based on the cationic oligomerization principle, and a complexed catalyst system is formed by using a Lewis acid-based catalyst and a promoter. The process of the inventive 1-decene oligomerization comprises:

reacting 1-decene in n-hexane as a solvent, in a volume ratio of 1-decene to n-hexane of 3:8-4:1 under a condition of a temperature of 80-120° C. and a pressure of 0.8-1.4 MPa for 5-6 hours;

stopping the reaction and removing the catalyst by filtration;

removing the solvent n-hexane by distillation under ambient pressure; and removing the unreacted monomer 1-decene and part of dimers by distillation under reduced pressure to produce the final oligomer.

DETAILED DESCRIPTION OF THE INVENTION

The present application will be further described based on the following examples.

Example 1

Acidification and Impregnation of a Sphere-Shaped Gamma-Alumina Carrier

A sphere-shaped gamma-alumina carrier, having a diameter of 1.3-2.3 mm, a specific surface area of 100-180 $m^2/g$ and a total pore volume of 1.0 ml/g or more, is impregnated in 1.0 M hydrochloric acid solution for 6 hours at room temperature, then vacuum dried at 80-100° C. for 12 hours and subsequently calcinated at a high temperature of 400° C. for 6 hours.

Immobilization of Aluminum Trichloride in a Solution:

Under the protection of argon, 5 g of anhydrous aluminum trichloride is dissolved in 100 ml of tetrachloromethane to prepare a solution, into which 10 g of the activated alumina carrier is added, refluxed at a reflux temperature for 24 hours before the solvent is removed, washed with n-hexane, and then vacuum dried to obtain the supported aluminum trichloride catalyst.

The chlorine content in the supported aluminum trichloride catalyst is measured, by Volhard titration, to be 8.56 wt %.

Catalysis of 1-Decene Oligomerization:

To a 250 ml high pressure kettle for polymerization, 80 ml of n-hexane, 8 g of catalyst obtained as above, 30 ml of 1-decene and 0.174 ml of water as a co-catalyst are added. 1-decene oligomerization is carried out under a condition of a temperature of 80° C. and a pressure of 1.0 MPa for 5 hours, after which the reaction is stopped and the catalyst is filtered out, the solvent n-hexane is removed by distillation under ambient pressure, and then unreacted monomer 1-decene and part of the dimers are removed by distillation under reduced pressure to produce the final oligomer. The conversion of 1-decene is 54.1 wt %. The oligomer has a kinematic viscosity at 40° C. of 16.51 $mm^2/s$, a kinematic viscosity at 100° C. of 5.81 $mm^2/s$ and a viscosity index of 208.80.

Example 2

The supported aluminum trichloride catalyst is prepared in the same manner as that in Example 1, except that a sphere-shaped gamma-alumina carrier is impregnated in a 1.5 M solution of hydrochloric acid for 6 hours at room temperature, then vacuum dried at 80-100° C. for 12 hours and subsequently calcinated at a high temperature of 400° C. for 6 hours.

The chlorine content in the supported aluminum trichloride catalyst is measured, by Volhard titration, to be 6.82 wt %.

Catalysis of 1-Decene Oligomerization:

To a 250 ml high pressure kettle for polymerization, 80 ml of n-hexane, 8 g of catalyst obtained as above, 30 ml of 1-decene and 0.14 ml of water as a co-catalyst are added. 1-decene oligomerization is carried out under a condition of a temperature of 80° C. and a pressure of 1.0 MPa for 5 hours, after which the reaction is stopped and the catalyst is filtered out, the solvent n-hexane is removed by distillation under ambient pressure, and then unreacted monomer 1-decene and part of the dimers are removed by distillation under reduced pressure to produce the final oligomer. The conversion of 1-decene is 57.1 wt %. The oligomer has a kinematic viscosity at 100° C. of 6.04 $mm^2/s$ and a viscosity index of 202.80.

Example 3

The supported aluminum trichloride catalyst is prepared in the same manner as that in Example 1, except that the carrier is calcinated at 800° C. for 6 hours.

The chlorine content in the supported aluminum trichloride catalyst is measured, by Volhard titration, to be 6.42 wt %.

Catalysis of 1-Decene Oligomerization:

To a 250 ml high pressure kettle for polymerization, 80 ml of n-hexane, 8 g of catalyst obtained as above, 30 ml of 1-decene and 0.13 ml of water as a co-catalyst are added. 1-decene oligomerization is carried out under a condition of a temperature of 80° C. and a pressure of 1.0 MPa for 5 hours, after which the reaction is stopped and the catalyst is filtered out, the solvent n-hexane is removed by distillation under ambient pressure, and then unreacted monomer 1-decene and part of the dimers are removed by distillation under reduced pressure to produce the final oligomer. The conversion of 1-decene is 57.4 wt %. The oligomer has a kinematic viscosity at 40° C. of 16.14 $mm^2/s$, a kinematic viscosity at 100° C. of 6.66 $mm^2/s$ and a viscosity index of 212.58.

Example 4

The supported aluminum trichloride catalyst is prepared in the same manner as that in Example 1, except that, in the immobilization of aluminum trichloride in a solution, 10 g of anhydrous aluminum trichloride is dissolved in 100 ml of tetrachloromethane to prepare a solution, into which 10 g of the activated alumina carrier is added, refluxed at a reflux temperature for 24 hours before the solvent is removed, washed with n-hexane, and then vacuum dried to obtain the supported aluminum trichloride catalyst.

The chlorine content in the supported aluminum trichloride catalyst is measured, by Volhard titration, to be 8.24 wt %.

Catalysis of 1-Decene Oligomerization:

To a 250 ml high pressure kettle for polymerization, 80 ml of n-hexane, 8 g of catalyst obtained as above, 30 ml of 1-decene and 0.167 ml of water as a co-catalyst are added. 1-decene oligomerization is carried out under a condition of a temperature of 80° C. and a pressure of 1.0 MPa for 5 hours, after which the reaction is stopped and the catalyst is filtered out, the solvent n-hexane is removed by distillation under ambient pressure, and then unreacted monomer 1-decene and part of the dimers are removed by distillation under reduced pressure to produce the final oligomer. The conversion of 1-decene is 58.6 wt %. The oligomer has a kinematic viscosity at 40° C. of 18.94 $mm^2/s$, a kinematic viscosity at 100° C. of 5.97 $mm^2/s$ and a viscosity index of 197.07.

Example 5

The supported aluminum trichloride catalyst is prepared in the same manner as that in Example 1, except that the carrier is calcinated at 600° C. for 6 hours.

The chlorine content in the supported aluminum trichloride catalyst is measured, by Volhard titration, to be 7.83 wt %.

Catalysis of 1-Decene Oligomerization:

To a 250 ml high pressure kettle for polymerization, 80 ml of n-hexane, 8 g of catalyst obtained as above, 30 ml of 1-decene and 0,159 ml of water as a co-catalyst are added. 1-decene oligomerization is carried out under a condition of a temperature of 80° C. and a pressure of 1.0 MPa for 5 hours, after which the reaction is stopped and the catalyst is filtered out, the solvent n-hexane is removed by distillation under ambient pressure, and then unreacted monomer 1-decene and part of the dimers are removed by distillation under reduced pressure to produce the final oligomer. The conversion of 1-decene is 52.4 wt %. The oligomer has a kinematic viscosity at 40° C. of 16.09 $mm^2/s$, a kinematic viscosity at 100° C. of 5.38 $mm^2/s$ and a viscosity index of 208.85.

Example 6

The supported aluminum trichloride catalyst is prepared in the same manner as that in Example 1, except that the carrier is calcinated at 600° C. for 12 hours.

The chlorine content in the supported aluminum trichloride catalyst is measured, by Volhard titration, to be 7.77 wt %.

Catalysis of 1-Decene Oligomerization:

To a 250 ml high pressure kettle for polymerization, 80 ml of n-hexane, 8 g of catalyst obtained as above, 30 ml of 1-decene and 0.159 ml of water as a co-catalyst are added. 1-decene oligomerization is carried out under a condition of a temperature of 80° C. and a pressure of 1.0 MPa for 5 hours, after which the reaction is stopped and the catalyst is filtered out, the solvent n-hexane is removed by distillation under ambient pressure, and the unreacted monomer 1-decene and part of the dimers are removed by distillation under reduced pressure to produce the final oligomer. The conversion of 1-decene is 57.8 wt %. The oligomer has a kinematic viscosity at 40° C. of 19.21 $mm^2/s$, a kinematic viscosity at 100° C. of 6.69 $mm^2/s$ and a viscosity index of 200.61.

Example 7

The catalyst, aluminum trichloride supported on a sphere-shaped gamma-alumina carrier, is prepared in the same manner as that in Example 1, except that the immobilization for aluminum trichloride lasts for 12 hours.

The chlorine content in the supported aluminum trichloride catalyst is measured, by Volhard titration, to be 7.92 wt %.

Catalysis of 1-Decene Oligomerization:

To a 250 ml high pressure kettle for polymerization, 80 ml of n-hexane, 8 g of catalyst obtained as above, 30 ml of 1-decene and 0.16 ml of water as a co-catalyst are added. 1-decene oligomerization is carried out under a condition of a temperature of 80° C. and a pressure of 1.0 MPa for 5 hours, after which the reaction is stopped and the catalyst is filtered out, the solvent n-hexane is removed by distillation under ambient pressure, and then unreacted monomer 1-decene and part of the dimers are removed by distillation under reduced pressure to produce the final oligomer. The conversion of 1-decene is 52.2 wt %. The oligomer has a kinematic viscosity at 40° C. of 15.17 $mm^2/s$.

Example 8

The supported aluminum trichloride catalyst is prepared in the same manner as that in Example 1, except that the gamma-alumina carrier is a strip-shaped carrier which has a diameter of 3 mm, a length of 4-10 mm, a specific surface area of 100-200 $m^2/g$ and a total pore volume of 0.6 ml/g or more, and the carrier is calcinated at 600° C. for 9 hours.

The chlorine content in the supported aluminum trichloride catalyst is measured, by Volhard titration, to be 7.87 wt %.

Catalysis of 1-Decene Oligomerization:

To a 250 ml high pressure kettle for polymerization, 80 ml of n-hexane, 8 g of catalyst obtained as above, 30 ml of 1-decene and 0.16 ml of water as a co-catalyst are added. 1-decene oligomerization is carried out under a condition of a temperature of 80° C. and a pressure of 1.0 MPa for 4 hours, after which the reaction is stopped and the catalyst is filtered out, the solvent n-hexane is removed by distillation under ambient pressure, and then unreacted monomer 1-decene and part of the dimers are removed by distillation under reduced pressure to produce the final oligomer. The conversion of 1-decene is 54.2 wt %. The oligomer has a kinematic viscosity at 100° C. of 4.95 $mm^2/s$ and a viscosity index of 222.14.

Example 9

The supported aluminum trichloride catalyst is prepared in the same manner as that in Example 1, except that the gamma-alumina carrier is a strip-shaped carrier which has a diameter of 3 mm, a length of 4-10 mm, a specific surface area of 100-200 $m^2/g$ and a total pore volume of 0.6 ml/g or more, and the immobilization for aluminum trichloride lasts for 12 hours.

The chlorine content in the supported aluminum trichloride catalyst is measured, by Volhard titration, to be 7.65 wt %

Catalysis of 1-Decene Oligomerization:

To a 250 ml high pressure kettle for polymerization, 80 ml of n-hexane, 8 g of catalyst obtained as above, 30 ml of 1-decene and 0.144 ml of water as a co-catalyst are added. 1-decene oligomerization is carried out under a condition of a temperature of 80° C. and a pressure of 1.0 MPa for 5 hours, after which the reaction is stopped and the catalyst is filtered out, the solvent n-hexane is removed by distillation under ambient pressure, and then unreacted monomer 1-decene and part of the dimers are removed by distillation under reduced pressure to produce the final oligomer. The conversion of 1-decene is 58.8 wt %. The oligomer has a kinematic viscosity at 40° C. of 14.82 mm$^2$/s.

Example 10

The catalyst, aluminum trichloride supported on a sphere-shaped gamma-alumina carrier, is prepared in the same manner as that in Example 1, except that a mixed solvent of tetrachloromethane and trichloromethane in volume ratio of 1:1 is used as the solvent in the immobilization for aluminum trichloride, and the immobilization lasts for 12 hours.

The chlorine content in the supported aluminum trichloride catalyst is measured, by Volhard titration, to be 8.11 wt %.

Catalysis of 1-Decene Oligomerization:

To a 250 ml high pressure kettle for polymerization, 80 ml of n-hexane, 8 g of catalyst obtained as above, 30 ml of 1-decene and 0.165 ml of water as a co-catalyst are added. 1-decene oligomerization is carried out under a condition of a temperature of 80° C. and a pressure of 1.0 MPa for 5 hours, after which the reaction is stopped and the catalyst is filtered out, the solvent n-hexane is removed by distillation under ambient pressure, and then unreacted monomer 1-decene and part of the dimers are removed by distillation under reduced pressure to produce the final oligomer. The conversion of 1-decene is 52.2 wt %. The oligomer has a kinematic viscosity at 40° C. of 16.87 mm$^2$/s.

Comparative Example 1

The catalyst, aluminum trichloride supported on a sphere-shaped gamma-alumina, is prepared in the same manner as that in Example 1, except that the carrier is not treated by the hydrochloric acid impregnation.

The chlorine content in the supported aluminum trichloride catalyst is measured, by Volhard titration, to be 6.33 wt %.

1-decene oligomerization is carried out in the same procedure and under the same conditions as those in Example 1.

The conversion of 1-decene is 35.0 wt %. The oligomer has a kinematic viscosity at 100° C. of 2.66 mm$^2$/s.

Comparative Example 2

The catalyst, aluminum trichloride supported on a sphere-shaped gamma-alumina, is prepared in the same manner as that in Example 1, except that the carrier is impregnated with 0.5 M hydrochloric acid for 2 hours.

The chlorine content in the supported aluminum trichloride catalyst is measured, by Volhard titration, to be 6.88 wt %.

1-decene oligomerization is carried out in the same procedure and under the same conditions as those in Example 1.

The conversion of 1-decene is 37.8 wt %. The oligomer has a kinematic viscosity at 100° C. of 2.46 mm$^2$/s.

Comparative Example 3

The supported aluminum trichloride catalyst is prepared in the same manner as that in Example 1, except that the sphere-shaped gamma-alumina carrier is impregnated in 0.5 M hydrochloric acid solution for 16 hours at room temperature, then vacuum dried at 80-100° C. for 12 hours and subsequently calcinated at a high temperature of 400° C. for 6 hours.

The chlorine content in the supported aluminum trichloride catalyst is measured, by Volhard titration, to be 7.45 wt %.

1-decene oligomerization is carried out in the same procedure and under the same conditions as those in Example 1.

The conversion of 1-decene is 52.11 wt %. The oligomer has a kinematic viscosity at 100° C. of 6.08 mm$^2$/s and a viscosity index of 172.00.

Comparative Example 4

The supported aluminum trichloride catalyst is prepared in the same manner as that in Example 1, except that the carrier is calcinated at 200° C.

The chlorine content in the supported aluminum trichloride catalyst is measured, by Volhard titration, to be 10.75 wt %.

1-decene oligomerization is carried out in the same procedure and under the same conditions as those in Example 1, except that water as a co-catalyst is used in an amount of 0.218 ml.

The conversion of 1-decene is 45.7 wt %. The oligomer has a kinematic viscosity at 100° C. of 4.13 mm$^2$/s.

Comparative Example 5

The supported aluminum trichloride catalyst is prepared in the same manner as that in Example 1, except that the carrier is calcined at 400° C. for 4 hours.

The chlorine content in the supported aluminum trichloride catalyst is measured, by Volhard titration, to be 7.26 wt %.

1-decene oligomerization is carried out in the same procedure and under the same conditions as those in Example 1, except that water as a co-catalyst is used in an amount of 0.147 ml.

The conversion of 1-decene is 47.7 wt %. The oligomer has a kinematic viscosity at 100° C. of 4.24 mm$^2$/s.

INDUSTRIAL APPLICABILITY

The supported catalyst according to the present application can be applied in the catalysis of 1-decene oligomerization to produce 1-decene oligomer. The principle is believed to be based on cationic oligomerization principle, and a complexed catalyst system is formed by using a Lewis acid-based catalyst and a promoter. The process of the inventive 1-decene oligomerization comprises: reacting 1-decene in n-hexane as a solvent, in a volume ratio of 1-decene to n-hexane of 3:8-4:1 under a condition of a temperature of 80-120° C. and a pressure of 0.8-1.4 MPa for 5-6 hours; stopping the reaction and removing the catalyst by filtration; removing the solvent n-hexane by distillation under ambient pressure; and removing the unreacted monomer 1-decene and part of the dimers by distillation under reduced pressure to produce the final oligomer. The conversion of 1-decene is 50 wt % or more. The oligomer has a kinematic viscosity at 40° C. of 6.0-25 mm$^2$/s and a viscosity index of 160-262.

The 1-decene oligomer produced according to the method of the present application satisfies the requirement for viscosity of lubricant base oil, resulting a high quality of the oil product.

The heterogeneous polymerization system according to the present application can reduce the chlorine content in the product, allow the catalyst to be separated and recycled from product, reducing pollution to environment.

What is claimed is:
1. A process for the synthesis of 1-decene oligomer comprising:

i) reacting 1-decene in the presence of aluminum trichloride supported on gamma-alumina carrier as a catalyst in n-hexane as a solvent in a volume ratio of 1-decene to n-hexane of 3:8-4:1, and in a weight ratio of the catalyst to 1-decene of 1:3 under a pressure of 0.8-1.4 MPa at a temperature of 80-120° C. for 5-6 hours;

ii) stopping the reaction and removing the catalyst by filtration, iii) removing the solvent n-hexane by atmospheric distillation under ambient pressure, and iv) removing unreacted monomer 1-decene and part of 1-decene dimers by distillation, under reduced pressure to produce 1-decene oligomer;

wherein the aluminum trichloride supported on gamma-alumina as a catalyst contains 6.42 wt % to 8.56 wt % of chlorine and is prepared by impregnating a sphere-shaped or strip-shaped gamma-alumina carrier in 0.5-2.0 M solution of hydrochloric acid, sulfuric acid, nitric acid or mixtures thereof for 4-12 hours, then vacuum drying at 80-100° C. for 2-12 hours and calcinating at 400-800° C. for 6-16 hours to provide an activated gamma-alumina carrier; and dissolving 5-10 g of anhydrous aluminum trichloride in 100 ml of an organic solvent selected from the group consisting of tetrachloromethane, trichloromethane and dichloromethane to prepare a solution, into which 10-20 g of the activated gamma-alumina carrier is added then refluxing at a reflux temperature for 6-24 hours, and further removing solvent, washing with n-hexane, and vacuum drying to obtain said catalyst.

2. The process according to claim 1, wherein the sphere-shaped or strip-shaped gamma-alumina carrier is acidified by using a hydrochloric acid having a concentration of 1 M for 6 hours, and calcinated at a calcination temperature of 400° C. for 12 hours.

3. The process according to claim 1, wherein the organic solvent for immobilizing anhydrous aluminum trichloride is tetrachloromethane or a mixed solvent of tetrachloromethane and trichloromethane in a volume ratio of 1:1, and the reflux lasts for a period of 12 hours.

4. The process according to claim 1, wherein the gamma-alumina carrier is a sphere-shaped gamma-alumina carrier having a diameter of 1.3-2.3 mm, a specific surface area of 100-180 $m^2$/g, and a total pore volume of 1.0 ml/g or more.

5. The process according to claim 1, wherein the gamma-alumina carrier is a strip-shaped gamma-alumina carrier having a length of 4-10 mm, a specific surface area of 100-200 $m^2$/g, and a total pore volume of 0.6 ml/g or more.

6. The process according to claim 1, wherein, all of the reactions, in the preparation of the aluminum trichloride supported on gamma-alumina as a catalyst, are carried out under protection of inert gas selected from the group consisting of nitrogen and argon.

* * * * *